United States Patent [19]  
Strikman

[11] Patent Number: 4,710,713  
[45] Date of Patent: Dec. 1, 1987

[54] NUCLEAR MAGNETIC RESONANCE SENSING APPARATUS AND TECHNIQUES

[75] Inventor: Shmuel Strikman, both of Rehovot, Israel

[73] Assignees: Numar Corporation, Malvern, Pa.; Zvi Taicher

[21] Appl. No.: 838,503

[22] Filed: Mar. 11, 1986

[51] Int. Cl.$^4$ ............................................. G01R 33/20
[52] U.S. Cl. ....................................... 324/303; 324/318
[58] Field of Search ............... 324/303, 306, 333, 336; 73/151

[56] References Cited

U.S. PATENT DOCUMENTS

| | | | |
|---|---|---|---|
| 3,213,357 | 10/1965 | Brown et al. | 324/303 |
| 3,483,465 | 12/1969 | Baker, Jr. | 324/303 |
| 3,597,681 | 8/1971 | Huckabay | 324/303 |
| 3,617,867 | 11/1971 | Herzog | 324/303 |
| 3,667,035 | 5/1972 | Slichter | 324/303 |
| 4,350,955 | 9/1982 | Jackson et al. | 324/303 |

FOREIGN PATENT DOCUMENTS 2141236 12/1984 United Kingdom .

OTHER PUBLICATIONS

A. Timur—"Pulsed Nuclear Magnetic Resonance Studies of Porosity, Movable Fluid, and Permeability of Sandstones," Journal of Petroleum Technology, Jun. 1969, p. 775.

R. C. Herrick, S. H. Couturie, D. L. Best—"An Improved Nuclear Magnetism Logging System and its Application to Formation Evaluation," SPE 8361 presented at the 54th Annual Fall Technical Conference and Exhibition of the SPE of AIME held in Las Vegas, NE, Sep. 23-26, 1979.

R. K. Cooper and J. A. Jackson—"Remote (Inside-Out) NMR.I. Remote Production of a Region of Homogeneous Magnetic Field," Journal of Magnetic Resonance, 41,400 (1980).

L. J. Burnett and J. A. Jackson,—"Remote (Inside-Out) NMR, II Sensitivity of NMR Detection for External Samples," Journal of Magnetic Resonance, 41,406 (1980).

J. A. Jackson, L. J. Burnett and J. F. Harmon,—"Remote (Inside-Out) NMR, III, Detection of Nuclear Magnetic Resonance in a Remotely Produced Region of Homogeneous Magnetic Field," Journal of Magnetic Resonance, 41,411 (1980).

C. P. Slichter—"Principles of Magnetic Resonance," Appendix G, Springer-Verlag, Berlin Heidelberg, New York, 1980.

Primary Examiner—Stewart J. Levy  
Assistant Examiner—Louis M. Arana  
Attorney, Agent, or Firm—Caesar, Rivise, Bernstein, Cohen & Pokotilow, Ltd.

[57] ABSTRACT

Nuclear magnetic resonance sensing apparatus including one or more magnets operative to generate a static magnetic field in a region remote therefrom containing materials sought to be analyzed, the one or more magnets defining a longitudinal axis, the static magnetic field having a static field direction substantially perpendicular to the longitudinal axis and having generally uniform amplitude along the azimuth with respect to the longitudinal axis in the remote region;

apparatus for generating a radio frequency magnetic field in the remote region for exciting nuclei of the material sought to be analyzed and having a radio frequency magnetic field direction substantially perpendicular to both the longitudinal axis and to the static field direction; and apparatus for receiving nuclear magnetic resonance signals from the excited nuclei and for providing an output indication of the properties of the material sought to be analyzed.

Methods for nuclear magnetic resonance sensing are also described and claimed.

26 Claims, 5 Drawing Figures

NUCLEAR MAGNETIC RESONANCE SENSING APPARATUS AND TECHNIQUES

FIELD OF THE INVENTION

The present invention relates to nuclear magnetic resonance sensing apparatus and techniques having particular application to sensing in a cylindrical volume surrounding a probe, inter alia in well logging.

BACKGROUND OF THE INVENTION

The description of this invention and its background will be approached in the context of well logging because well logging is a known application of the invention. There is no intention to limit the generality of the present invention to the field of well logging.

Fluid flow properties of porous media have long been of interest in the oil industry. A. Timur, in "Pulsed Nuclear Magnetic Resonance Studies of Porosity, Movable Fluid, and Permeability of Sandstones," Journal of Petroleum Technology, June 1969, p.775, proved experimentally that NMR methods provide a rapid nondestructive determination of porosity, movable fluid, and permeability of rock formation.

It is known that when an assembly of magnetic moments such as those of hydrogen nuclei are exposed to a static magnetic field they tend to align along the direction of the magnetic field, resulting in bulk magnetization. The rate at which equilibrium is established in such bulk magnetization upon provision of the state magnetic field is characterized by the parameter T 1, the spin-lattice relaxation time.

It has been observed that the mechanism which determines the value of T 1 depends on molecular cynamics. In liquids, molecular dynamics is a function of molecular size and intermolecular interactions. Therefore, water and different types of oil have different T 1 values.

In a heterogeneous medium such as porous solid which contains liquid in its pores, the dynamics of the molecules close to the solid surface are also significant and differ from the dynamics of the bulk liquid. It may thus be appreciated that the T 1 parameter provides valuable information relating to well logging parameters.

There exist a number of techniques for disturbing the equilibrium of an assembly of magnetic moments such as those of hydrogen nuclei, for T 1 parameter measurements. One such technique is exemplified by the Schlumberger Nuclear Magnetic Logging Tool.

The Schlumberger Nuclear Magnetic Logging (NML) tool is described in R. C. Herrick, S. H. Courturle, and D. L. Best, "An Improved Nuclear Magnetic Logging System and its Application to Formation Evaluation," PE 8361 presented at the 54th Annual Fall Technical Conference and Exhibition of the Society of Petroleum Engineers of AIME, held in Las Vegas Nevada, Sept. 23–26, 1979 and in R. J. S. Brown et al. U.S. Pat. No. 3,213,357, entitled, "Earth formation and fluid material investigation by nuclear magnetism relaxation rate determination".

The Schlumberger Nuclear Magnetic Logging (NML) tool measures the free precession of proton nuclear magnetic moments in the earth's magnetic field by applying a relatively strong DC polarizing field to the surrounding rock formation in order to align proton spins approximately perpendicular to the earth's magnetic field. The polarizing field must be applied for a period roughly five times T1 (the spin-lattice relaxation time) for sufficient polarization (approximately 2 seconds). (See the Herrick et al. reference mentioned above.) At the end of polarization, the field is turned off rapidly. Since the proton spins are unable to follow this sudden change, they are left aligned perpendicular to the earth's magnetic field and precess about this field at the Larmor frequency corresponding to the local earth's magnetic field (roughly from 1300 to 2600 Hz, depending on location).

The spin precession induces, in a pickup coil, a sinusoidal signal whose amplitude is proportional to the density of protons present in the formation. The signal decays with a time constant T2* (transverse relaxation time) due to inhomogeneities in the local magnetic field over the sensing volume.

Hydrogen protons in solids or bound to surfaces have very short characteristic relaxation times T 1, however bulk fluids in pore spaces have much longer relaxation times. In view of the fact that the observed decay with a relaxation time constant T 2* is less than or equal to T 1, the Schlumberger NML tool is blind to matrix and bound protons by delaying observation of the signal until 20–30 milliseconds after the beginning of decay. T 1 measurements can be performed by comparison of free precession following polarizing pulses of differing duration. Because the large polarizing field cannot be turned off instantly, much of the signal amplitude is lost.

At present there are two ways to compensate for this effect:

1. U.S. Pat. No. 3,483,465, to J. M. Baker, entitled "Nuclear magnetic logging system utilizing an Oscillated Polarizing Field," employs a polarizing field which is allowed to oscillate at the Larmor frequency corresponding to the earth's magnetic field for a few cycles.

2. U.S. Pat. No. 3,667,035, to Slichter, entitled "Nuclear Magnetism Logging," describes applying an alternating magnetic field in a direction transverse to the earth's magnetic field and at a frequency corresponding to the Larmor precession frequency corresponding to the earth's magnetic field.

Although there have been major improvements in the Schlumberger nuclear magnetic logging (NML) technique during the last 25 years, the following disadvantages have not yet been overcome:

1. Species with short relaxation time (shorter than 20–30 msec) cannot be detected by the Schlumberger NML technique due to long dead time of the system following the polarizing DC pulse.

2. The Schlumberger NML technique involves the suppression of a very high undesired signal coming from the bore fluid (which is in close proximity to the probe) and requires doping of the bore fluid with paramagnetic materials. This process is costly and time consuming.

3. The Schlumberger NML technique cannot carry out a T 1 (spin-lattice relaxation time) measurement at a commercially operational logging speed due to the long time required for each single T 1 measurement.

Another technique for nondestructive determination of porosity, movable fluid, and permeability of rock formation is the Los Alamos NMR technique described in the following publications:

R. K. Cooper and J. A. Jackson "Remote (Inside-Out) NMR.I Production of a Region of Homogenous Magnetic Field," J. Magn. Reson. 41, 400 (1980);

L. J. Burnett and J. A. Jackson, "Remote (Inside-Out) NMR. II Sensitivity of NMR Detection for External Samples," J. Magn. Reson. 41, 406(1980);

J. A. Jackson, L. J. Burnett and J. F. Harmon, "Remote (Inside-Out) NMR. III Detection of Nuclear Magnetic Resonance in a Remotely Produced Region of Homogeneous Magnetic Field," J. Magn. Reson. 41, 411 (1980);

U.S. Pat. No. 4,350,955, to J. A. Jackson et al., entitled "Magnetic Resonance Apparatus."

The Los Alamos NMR technique is based on the development of a new type magnet/RF coil assembly. This allows one to obtain the NMR signal mostly from a torioidal "doughnut"-shaped region in the surrounding rock formation at a specified distance from the bore hole axis.

The Los Alamos approach is based on T 1 measurements only, which are achieved by standard pulse NMR techniques which allow one to overcome one of the difficulties noted above in connection with the Schlumberger technique, i.e. the problem of the long dead time. However, it does not eliminate the bore fluid signal problem nor does it overcome the difficulty of unacceptably low operational speeds due to low signal to noise ratio. Jackson proposes to increase significantly the static magnetic field strength but admits that this is impractical at the present state of magnet technology.

A basic difficulty with the Los Alamos approach of Jackson lies in the fact that there is defined a "doughnut"-shaped region having high homogeneity whose location and field strength tend to vary over time during operation due in part to changes in the local earth's magnetic field, temperature, and mechanical parameters of the field producing apparatus. The Los Alamos approach, employing an antenna which is tuned to a fixed frequency, lacks the flexibility to resonantly match the changing field.

A similar difficulty is encountered using a technique described in U.K. Patent Application No. 2,141,236A, published Dec. 12, 1984, entitled "Nuclear Magnetic Logging".

Another basic difficulty associated with any technique wherein a relatively small size, high homogeneity region is examined lies in the fact that each single measurement of the decay process must have a duration approximately as long as the relevant relaxation time. The tool must be present in the local region of measurement throughout this duration, thus restricting the logging operation to non-economical logging speeds.

SUMMARY OF THE INVENTION

The present invention seeks to provide nuclear magnetic resonance (NMR) apparatus having performance which is significantly improved over that of the prior art, and yields additional operational possibilities not available to previous apparatus and techniques. The improvements produced by the present invention lie both in reducing spurious signals and in significantly enhanced signal to noise ratios. Additional operational possibilities include two dimensional imaging and measurements of diffusion coefficient of the fluid in the rock formation.

There is thus provided in accordance with a preferred embodiment of the invention, nuclear magnetic resonance sensing apparatus including one or more magnets operative to generate a static magnetic field in a region remote therefrom containing materials sought to be analyzed, the one or more magnets defining a longitudinal axis and being magnetized in a magnetization direction extending generally perpendicularly to the longitudinal axis, apparatus for generating a radio frequency magnetic field in said remote region for exciting nuclei of the material sought to be analyzed and including at least one coil wound in a manner whereby the coil turns lie in planes substantially parallel to planes containing the magnetization direction and the longitudinal axis, and receiving apparatus for receiving nuclear magnetic resonance signals from the excited nuclei and for providing an output indication of the properties of the material sought to be analyzed.

There is also provided in accordance with a preferred embodiment of the present invention, well logging apparatus for geophysical examination of a bore hole including apparatus for generating a static magnetic field in a remote region containing materials sought to be analyzed comprising at least one permanent magnet defining a longitudinal axis for generating a static magnetic field having a static field direction substantially perpendicular to the longitudinal axis in the remote region, apparatus for generating a radio frequency (RF) magnetic field in the same remote region for exciting nuclei of the material sought to be analyzed and having a radio frequency magnetic field direction substantially perpendicular to both the longitudinal axis and to the static field direction, and receiving apparatus for receiving nuclear magnetic resonance signals from the excited nuclei and for providing an output indication of the properties of the material sought to be analyzed.

Further in accordance with a preferred embodiment of the present invention, the apparatus for generating a static magnetic field includes apparatus for generating a static magnetic field in the vicinity of a well bore hole.

Further in accordance with an embodiment of the invention, the one or more permanent magnets comprise at least one permanent magnet having substantially uniform magnetization in a magnetization direction extending generally along an axis perpendicular to said longitudinal axis.

According to an alternative embodiment of the invention, an equivalent electromagnet or electromagnets may be employed in place of the at least one permanent magnet.

Additionally in accordance with a preferred embodiment of the present invention, the apparatus for generating a static magnetic field includes apparatus for generating a static magnetic field having a magnetic field amplitude gradient which extends substantially radially with respect to the longitudinal axis and which gradient is substantially azimuthally symmetric about the longitudinal axis.

Further in accordance with a preferred embodiment of the invention there is provided means for varying the RF frequency over a given range in order to provide a scanning function during operation.

As a result, varying the RF frequency over a given range can provide spatial resolution in the direction perpendicular to the axis of the bore hole. Furthermore, at a given frequency, substantially all the material sought to be analyzed experiences the same static magnetic field amplitude gradient, providing direct diffusion coefficient measurements in the fluid as described by C. P. Slichter in "Principles of Magnetic Resonance," Appendex G, Springer-Verlag, Berlin Heidelberg, New York, 1980.

Further in accordance with a preferred embodiment of the invention there is provided nuclear magnetic resonance sensing apparatus including one or more ferrite permanent magnets operative to generate a static magnetic field in a remote region containing materials sought to be analyzed, one or more ferrite permanent magnets of generally cylindrical configuration and defining a longitudinal axis with an overall length greater than the radial separation of the remote region and the longitudinal axis, and one or more ferrite permanent magnets having substantially uniform magnetization in a direction extending generally along a magnetization axis perpendicular to the longitudinal axis, apparatus for generating a radio frequency magnetic field in the remote region for exciting nuclei of the material sought to be analyzed, the apparatus for generating including one or more coil wound about the surface of the one or more ferrite permanent magnets whereby the coil turns lie in planes substantially parallel to a plane containing the magnetization axis and the longitudinal axis, and receiving apparatus for receiving, via the one or more coil, nuclear magnetic resonance signals from the materials to be analyzed and for providing an output indication of the properties of the material sought to be analyzed.

Further in accordance with a preferred embodiment of the invention there is provided a method for nuclear magnetic resonance sensing providing one or more magnets defining a longitudinal axis and having substantially uniform magnetization and a magnetization direction along an axis perpendicular to the longitudinal axis, causing the one or more magnets to generate a static magnetic field of generally uniform amplitude in a remote region containing materials sought to be analyzed, the static magnetic field having a static field direction perpendicular to the longitudinal axis in the remote region, generating a radio frequency magnetic field in the remote region for exciting nuclei of the material sought to be analyzed and having a radio frequency magnetic field direction substantially perpendicular to both the longitudinal axis and to the static field direction, receiving nuclear magnetic resonance signals from the excited nuclei, and providing in response to the received nuclear magnetic resonance signals an output indication of the properties of the material sought to be analyzed.

Further in accordance with a preferred embodiment of the invention there is provided apparatus for well logging using nuclear magnetic resonance and generating a static magnetic field substantially perpendicular to the axis of a bore hole in a region surrounding the bore hole that includes material sought to be analyzed, generating a radio frequency (RF) magnetic field in the region in a direction substantially perpendicular to both the axis of the bore hole and to the static magnetic field for exciting nuclei of the material sought to be analyzed, and receiving nuclear magnetic resonance signals from the excited nuclei.

BRIEF DESCRIPTION OF THE DRAWINGS

The present invention will be understood and appreciated more fully from the following detailed description taken in conjunction with the drawings in which.

DETAILED DESCRIPTION OF THE INVENTION

Figure 1:
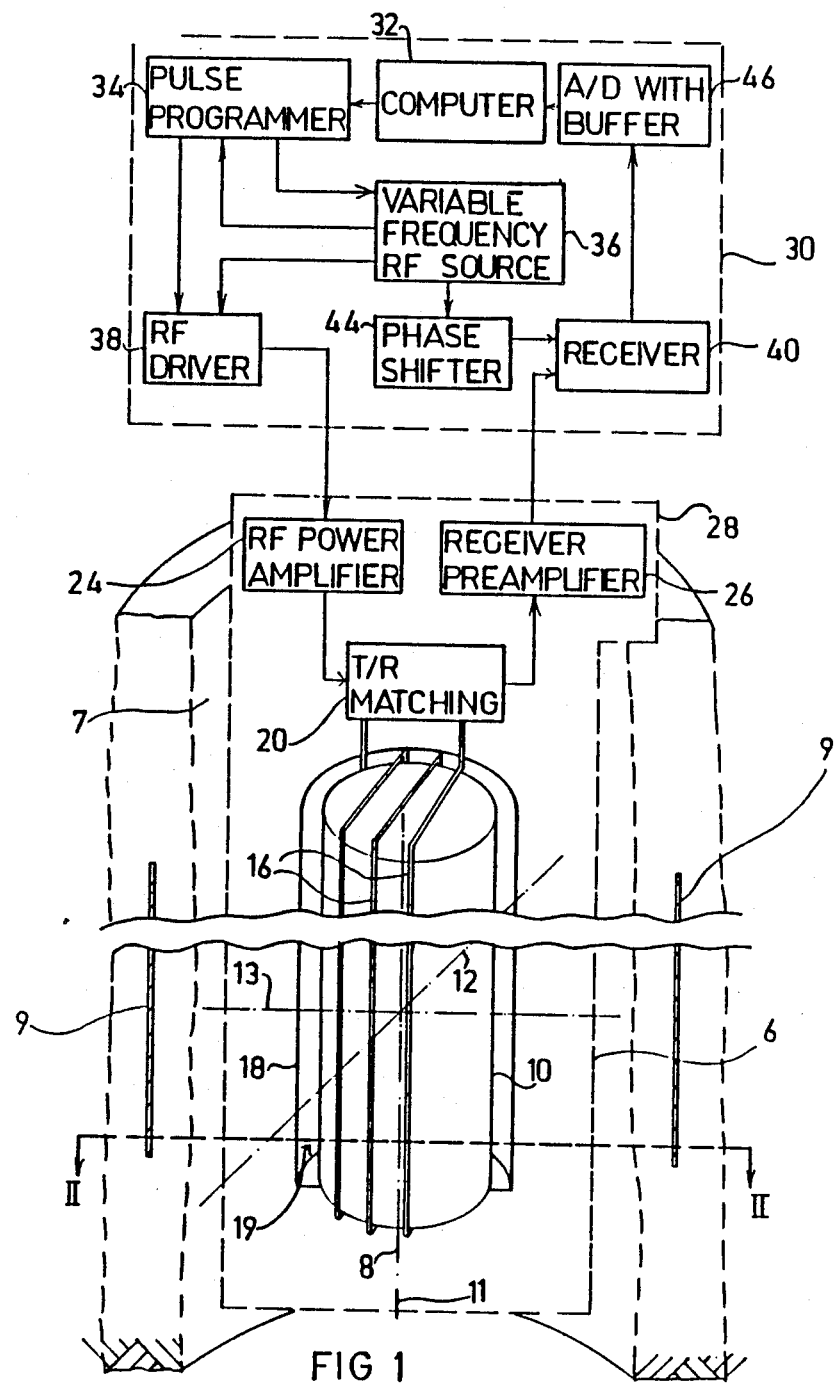
FIG. 1 is a partly pictorial and partly block diagram illustration of well logging apparatus constructed and operative in accordance with a preferred embodiment of the present invention.

Reference is now made to FIG. 1, which illustrates in general form, well logging apparatus constructed and operative in accordance with a preferred embodiment of the invention disposed in a portion of a bore hole. The apparatus includes a first portion 6, which is arranged to be lowered into a bore hole 7 having a bore hole longitudinal axis 8 in order to examine the nature of materials in the vicinity of the bore hole lying in a region 9 of generally cylindrical configuration spaced from and surrounding the bore hole.

The first portion 6 preferably comprises a generally cylindrical permanent magnet 10, preferably having a circular cross section and arranged along a permanent magnet longitudinal axis 11 which is preferably coaxial with the longitudinal axis 8 of the bore hole. According to an alternative embodiment of the invention a plurality of permanent magnets 10 may be employed. Through the specification, the one or more permanent magnets 10 will be considered together and referred to as permanent magnet 10 and their common longitudinal axis will be identified as longitudinal axis 11.

It is essential that the permanent magnet 10 have an overall length along its longitudinal axis which is greater than the dimensions of the permanent magnet 10 in directions perpendicular to the longitudinal axis. Furthermore, the overall length of the permanent magnet is greater than the diameter of the region 9.

Permanent magnet 10 perferably has uniform magnetization substantially along the permanent magnet magnetization axis 12 perpendicular to the longitudinal axis 11 of the bore hole. The permanent magnet is typically formed of a ferrite permanent material such as Arnox or Permadure. It is essential that the permanent magnet material be non-conductive.

The first portion 6 also comprises one or more coil windings 16 which preferably are arranged on the permanent magnet surface such that each coil turn lies in a plane substantially parallel to a plane containing permanent magnet magnetization axis 12 and longitudinal axis 11. Specifically, the axis 13 of the coil windings 16 is substantially perpendicular to both longitudinal axis 11 of the bore hole and axis 12 of the permanent magnet magnetization.

It is essential that the coil windings 16 have an overall length parallel to the longitudinal axis 11 which is greater than the dimensions of the coil windings 16 parallel to the magnetization axis 12. Furthermore, the overall length of the coil windings 16 parallel to the longitudinal axis 11 is approximately equal to the overall permanent magnet length along the same axis. As a consequence the overall length of the coil windings 16 parallel to the longitudinal axis 11 is greater than the diameter of the region 9.

The permanent magnet 10 and coil windings 16 are preferably housed in a non-conductive, non-ferromagnetic protective housing 18. The housing and its contents hereinafter will be referred to as a probe 19.

The coil windings 16, together with a transmitter/receiver (T/R) matching circuit 20 define a transmitter/receiver (T/R) circuit. T/R matching circuit 20 typically includes a resonance capacitor, a T/R switch and both to-transmitter and to-receiver matching circuitry and is coupled to a RF power amplifier 24 and to a receiver preamplifier 26.

Disposed in a housing indicated by block 30 is control circuitry for the logging apparatus including a computer 32, which provides a control output to a pulse programmer 34 which receives an RF input from a variable frequency RF source 36. Pulse programmer 34 controls the operation of the variable frequency RF source 36 as well as an RF driver 38, which receives an input from variable frequency RF source 36 and outputs to RF power amplifier 24.

The output of RF receiver preamplifier 26 is supplied to an RF receiver 40 which receives an input from a phase shifter 44. Phase shifter 44 receives an input from variable frequency RF source 36. Receiver 40 outputs via an A/D converter with a buffer 46 to computer 32 for providing desired well logging output data for further use and analysis.

All of the elements described hereinabove which are normally contained in housing 28 and/or housing 30 may be located either above ground or alternatively may be passed through the bore hole.

METHODS AND MEASURING TECHNIQUES

According to a preferred embodiment of the present invention, the length of the probe 19 in a direction parallel to the longitudinal axis 11 is greater than its dimensions in planes perpendicular to longitudinal axis 11. Thus, the cross sectional configuration of probe 19 is identical at all locations therin along the longitudinal axis 11 except at the ends of the probe.

Therefore to obtain maximum logging efficiency and speed, it is desired to employ a probe of the maximum practicable length along longitudinal axis 11 such that a maximum volume of materials is sensed simultaneously providing a consequently maximum signal to noise result.

Figure 2:
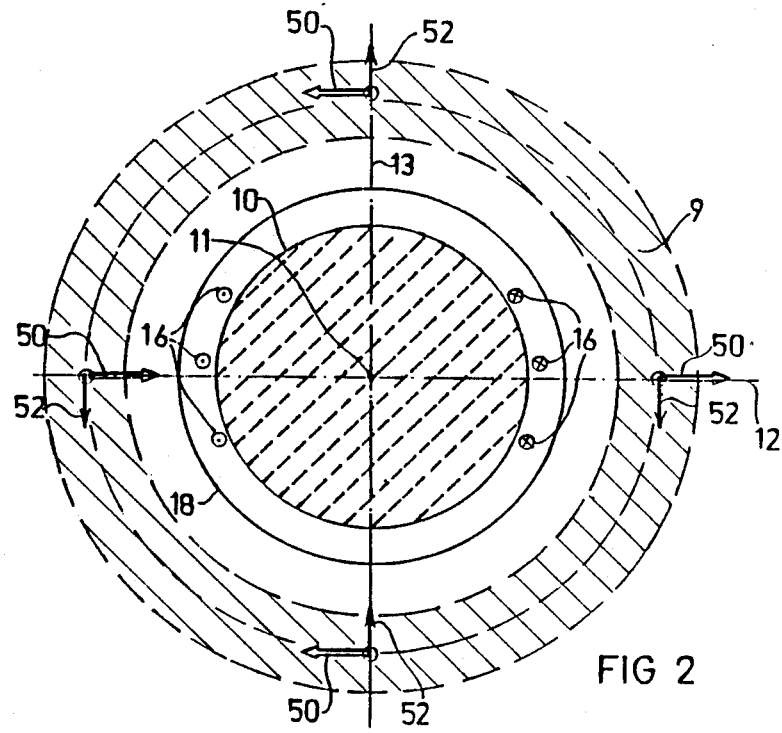
FIG. 2 is a sectional illustration of the apparatus of FIG. 1 taken in a plane perpendicular to the axis of the bore hole indicated by the lines II—II in FIG. 1 and illustrating the arrangements of the static and radio frequency magnetic fields.

Reference is now made to FIG. 2, which illustrates the magnetic field direction arrangement of the static magnetic field (Arrows 50) and the RF magnetic field (Arrows 52) in the region 9 (FIG. 1) containing materials sought to be analyzed.

In well logging applications of the present invention, it is preferred that the static magnetic field amplitude and amplitude gradient be uniform along the azimuth defined about the longitudinal axis 11. The static magnetic field amplitude gradient is directed radially inward towards longitudinal axis 11. As a result, if one ignores end effects, there exists only one cylindrical region outside of the permanent magnet 10 which has a given static magnetic field amplitude.

It follows from this particular feature that stray resonance signals from diverse materials, such as drilling mud, outside of the defined cylindrical region do not participate in the NMR measurements.

Undesired end effects may be eliminated by employing a coil somewhat shorter, along longitudinal axis 11 than the permanent magnet 10, in order not to excite materials at the extreme longitudinal ends of the static magnetic field.

A useful feature resulting from the radially extending, azimuthally uniform static magnetic field amplitude gradient is that at different frequencies of the RF magnetic field, different cylindrical regions 9 (FIG. 1) at different radial separations from longitudinal axis 11 are subject to NMR excitation. This feature enables regions at differing radial separations from the longitudinal axis to be scanned by varying the RF magnetic field frequency. This provides an additional dimension to the conventional one dimensional scanning along longitudinal axis 11 by moving the probe 19 axially therealong.

All the nuclear moments in the material to be analyzed are aligned in the direction of the static magnetic field generated by the permanent magnet 10. According to a preferred embodiment of the present invention, the direction of the Rf magnetic field is substantially perpendicular to the static magnetic field at any point in the region 9. Such a field arrangement is conventional for NMR experiments and can be used for exciting nuclear bulk magnetization.

In accordance with the preferred embodiment, the materials to be analyzed experience a gradient of the magnetic field amplitude. A spin-echo pulse NMR technique is employed to obtain T 1 information which is a major objective of the present invention. The use of pulse NMR provides relatively short dead time and thus increases the sensitivity of the apparatus in measurements of fluids having short relaxation times which is correlated to small pore sizes. In addition, the short dead time increases measurement efficiency.

Another major advantage of the present invention is the presence of a constant static magnetic field amplitude and amplitude gradient in the materials to be analyzed over the measurement region 9. This feature is used for direct measurement of the diffusion coefficient of the liquid in the material to be analyzed as explained in C. P. Slichter in "Principles of Magnetic Resonance" Appendix G, Springer - Verlag Berlin Heidelberg, New York, 1980. This information has value in distinguishing different types of oil based on their relative viscosity. In addition the parameter T2, the transverse relaxation time, can be also derived from a spin-echo experiment.

The gradient of the static magnetic field can be utilized for radial flow measurements by exciting the nuclei at a first given frequency and receiving the NMR signal at a different frequency. This is the equivalent of exciting the nuclei at one radial location and receiving the signal therefrom at another radial location.

Figures 3A, 3B:
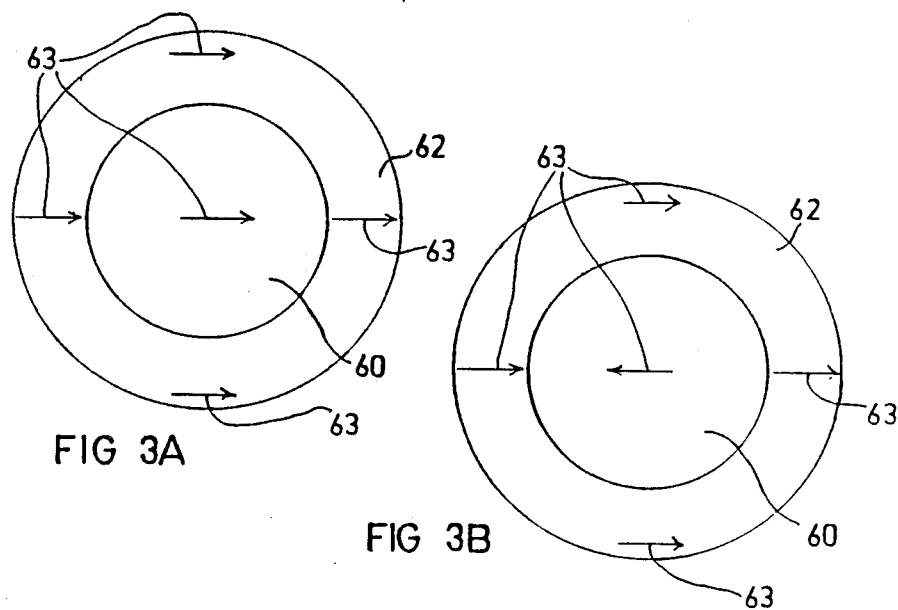
FIGS. 3A and 3B are simplified illustrations (not drawn to scale) of the type appearing in FIG. 2 which show the field arrangements during "on" and "off" portions of the operation cycle of the apparatus.

Reference is now made to FIGS. 3A and 3B which illustrate a preferred embodiment of the construction of the permanent magnet 10. The permanent magnet is formed of two concentric cylinders, formed of the same material having the same magnetization, and including an inner cylinder 60 and an outer cylinder 62, which have generally the same cross sectional areas. Using this construction and varying the relative rotational orientations of the two cylinders, the total static magnetic field produced by the combination of cylinders 60 and 62 may be varied between 0 and full magnetic field strength.

FIG. 3A illustrates the orientation of cylinders 60 and 62 wherein the magnetization thereof lies in the same direction, producing a full strength magnetic field in the surrounding vicinity. FIG. 3B illustrates the orientation of cylinders 60 and 62 wherein cylinder 60 is rotated by 180 degrees with respect to its orientation in FIG. 3A. Thus the magnetization of cylinder 60 lies in a direction opposite to the magnetization of cylinder 62. Due to the generally equal cross sectional areas of the two cylinders, a zero field results in the surrounding vicinity.

The construction of FIGS. 3A and 3B is particularly useful for transporting the permanent magnets.

It is a particular feature of the present invention that by varying the relative rotational orientation of the two cylinders 60 and 62 and by adjusting the azimuthal orientation of the coil 16, the static magnetic field strength can be varied, thus enabling differing regions to be analyzed while using the same RF frequency. The use of such a technique enables mapping at various radial distances from a given location along the bore hole.

Figure 4:
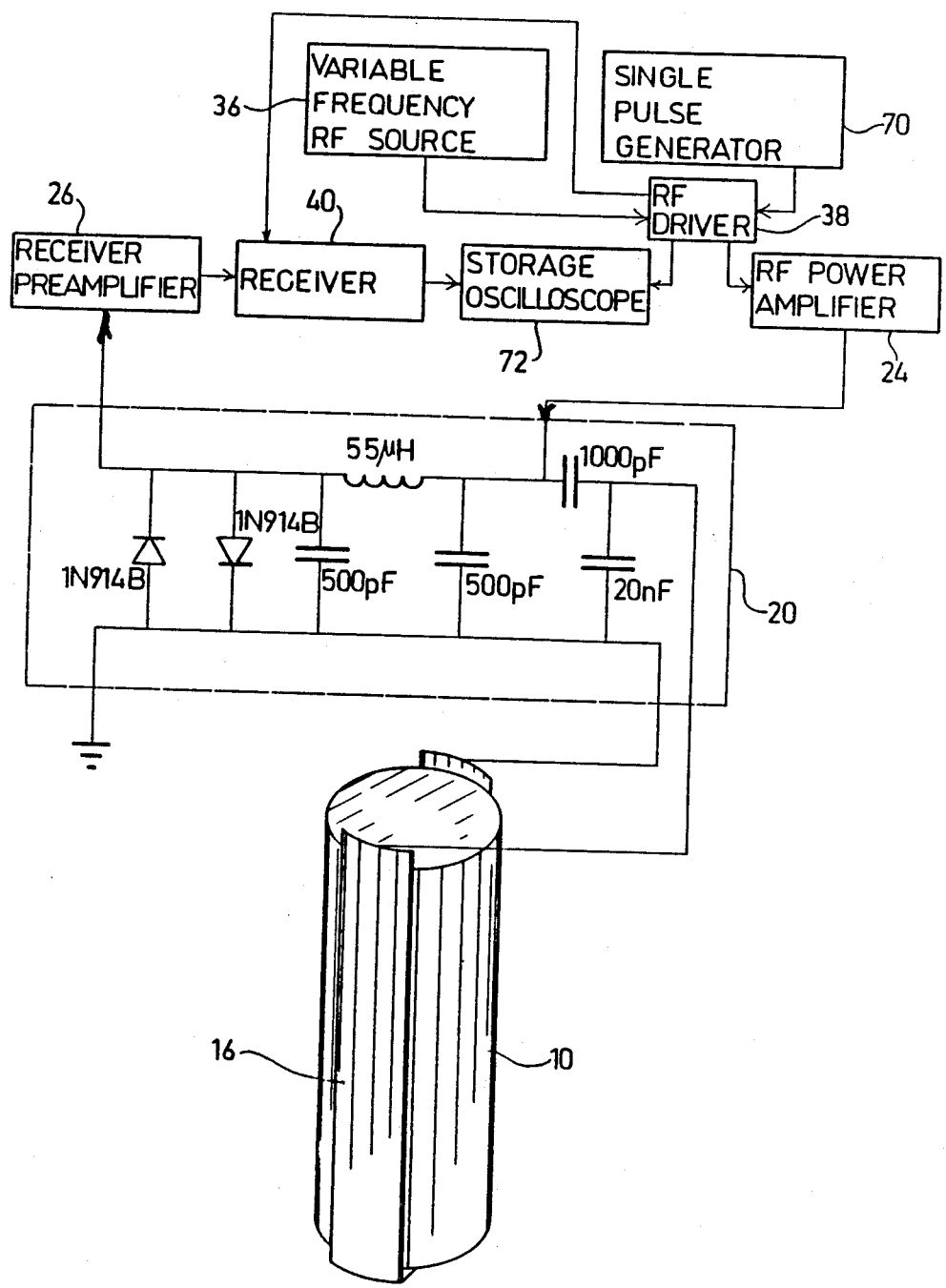
FIG. 4 is a partially block diagram, partially schematic and partial pictorial illustration of well logging apparatus constructed and operative in an experimental embodiment.

Reference is now made to FIG. 4 which illustrates an experimental setup employed in reducing the present invention to practice and confirming its efficacy.

A generally cylindrical ferrite permanent magnet 10 formed of a collection of discrete magnet elements and having a diameter of 127 mm and a length of 1440 mm is employed. A single winding coil 16, formed of lead, approximately 3 mm thick and defining a 70 degree opening is disposed about the magnet 10, as illustrated so as to lie in a plane containing the magnetization direction of the magnet 10 and the longitudinal axis thereof.

Coupled to the coil 16 is T/R matching circuitry 20, which includes diodes, capacitors and an inductance having the values indicated. T/R matching circuitry 20 receives an input from RF Power amplifier 24 which is typically a Matec Model 350, manufactured and sold by Matec Instruments, INC., a subsidiary of Matec, 60 Montebello Road, Warwick, RI 02886, USA.

An RF driver 38, which, in this embodiment comprises a Matec Model 410 pulse programmer, receives inputs from a single pulse generator 70, here a Wavetek Model 275, manufactured and sold by Wavetek San Diego, Inc. 9045 Balboa Ave., San Diego, CA 92123, USA., and from a variable frequency RF source 36, here a Matec Model 110.

RF driver 38 provides a reference output to a receiver 40, here a Matec Model 605, which receives a signal input from a receiver preamplifier 26, here a Matec 253. The receiver preamplifier, is coupled to the T/R matching circuitry 20, as shown. Receiver 40 outputs, in this experimental embodiment to a storage oscilloscope 72, such as a Gould Model 4035.

RF driver 38 also provides a trigger output to storage oscilloscope 72 and a pulse output to RF power amplifier 24.

Experimental spin-echo NMR tests run on the above-described apparatus on water samples of varying salinity and combinations of sand and water in the region sought to be analyzed indicated a signal to noise ratio for an NMR echo in accord with independent analysis of the material.

It will be appreciated by persons skilled in the art that the present invention is not limited to what has been particularly shown and described hereinabove. Rather the scope of the present invention is defined only by the claims which follow:

We claim:

1. Nuclear magnetic resonance sensing apparatus comprising:
    at least one magnet operative to generate a static magnetic field in a region remote therefrom containing materials sought to be analyzed, said at least one magnet having a longitudinal axis and having a magnetization direction extending substantially perpendicularly to said longitudinal axis;
    means for generating a radio frequency magnetic field in said remote region for exciting nuclei of the material sought to be analyzed and including at least one coil wound in a manner whereby the coil turns lie in planes substantially parallel to said magnetization direction and said longitudinal axis; and
    receiving means for receiving nuclear magnetic resonance signals from the excited nuclei and for providing an output indication of properties of the material sought to by analyzed.

2. Apparatus according to claim 1 and wherein said means for generating includes means for generating a static magnetic field in a well bore hole.

3. Apparatus according to claim 2 and also comprising means for displacing said means for generating a static magnetic field, means for generating a radio frequency magnetic field and receiving means along a bore hole, thereby to enable a plurality of nuclear magnetic resonance measurements to be carried out therealong.

4. Apparatus according to claim 1 and also comprising means for selectably varying the frequency of said radio frequency magnetic field.

5. Apparatus according to claim 1 and wherein said at least one magnet comprises at least one permanent magnet having substantially uniform magnetization in a magnetization direction extending generally along an axis perpendicular to said longitudinal axis.

6. Apparatus according to claim 1 and wherein said means for generating a static magnetic field includes means for generating a static magnetic field having a magnetic field amplitude gradient which extends substantially radially with respect to the longitudinal axis and which gradient is substantially azimuthally symmetric about the longitudinal axis.

7. Apparatus according to claim 6 and also comprising means for selectably varying the frequency of said radio frequency magnetic field and wherein said means for receiving is operative to receive nuclear magnetic resonance signals from the excited nuclei from a location different from that at which the nuclei were excited, thereby providing flow measurements.

8. Apparatus according to claim 1 and wherein said at least one magnet comprises a hollow cylindrical magnet and a cylindrical magnet which is located therewithin.

9. Apparatus according to claim 8 and also including means for varying the static magnetic field to permit NMR measurements at different radial distances from a given location comprising means for providing desired relative rotation of coaxial portions of said at least one magnet.

10. Well logging apparatus for geophysical examination of a bore hole comprising:
    means for generating a static magnetic field in the vicinity of a bore hole including at least one permanent magnet having its axis of magnetization disposed substantially perpendicular to the axis of the bore hole for generating a static magnetic field substantially perpendicular to the axis of the bore hole in a region surrounding the bore hole which region includes material sought to be analyzed;
    means for generating a radio frequency magnetic field in said region in a direction substantially perpendicular to both the axis of the bore hole and to the static magnetic field for exciting nuclei of the material sought to be analyzed; and receiving means for receiving nuclear magnetic resonance signals from the excited nuclei and for providing an output indication of properties of the material sought to be analyzed.

11. Apparatus according to claim 10 and wherein said means for generating a static magnetic field includes means for generating a static magnetic field having a magnetic field amplitude gradient which extends substantially radially with respect to the longitudinal axis and which gradient is substantially azimuthally symmetric about the longitudinal axis.

12. Apparatus according to claim 10 and also comprising means for varying the frequency of the radio frequency magnetic field to permit NMR measurements at different radial distances from a given borehole location.

13. Apparatus according to claim 12 and wherein at least one magnet defines relatively rotatable coaxial portions and means for providing desired relative rotation of said coaxial portions of said at least one magnet.

14. Nuclear magnetic resonance sensing apparatus comprising:

at least one ferrite permanent magnet operative to generate a static magnetic field in a region remote therefrom containing materials sought to be analyzed, said at least one ferrite permanent magnet being of generally cylindrical configuration and having a longitudinal axis, the overall length of said at least one ferrite permanent magnet along said longitudinal axis being greater than its dimensions perpendicular to said longitudinal axis and greater than twice the radial separation of said remote region and said longitudinal axis, said at least one ferrite permanent magnet having substantially uniform magnetization in a direction extending substantially along a magnetization axis perpendicular to said longitudinal axis;

means for generating a radio frequency magnetic field in said remote region for exciting nuclei of the material sought to be analyzed, said means for generating comprising at least one coil wound about the surface of said at least one ferrite permanent magnet whereby the coil turns lie in planes substantially parallel to said magnetization axis and said longitudinal axis; and receiving means for receiving, via said at least one coil, nuclear magnetic resonance signals from the materials to be analyzed and for providing an output indication of properties of the material sought to be analyzed.

15. Apparatus according to claim 14 and wherein said at least one ferrite permanent magnet has an overall configuration of a circular cylinder.

16. Apparatus according to claim 14 and wherein said at least one coil is wound along the surface of said at least one ferrite permanent magnet.

17. Apparatus according to claim 14 and also comprising means for displacing said means for generating a static magnetic field, means for generating a radio frequency magnetic field and receiving means along a bore hole, thereby to enable a plurality of nuclear magnetic resonance measurements to be carried out therealong.

18. Apparatus according to claim 14 and also comprising means for selectably varying the frequency of said radio frequency magnetic field.

19. A method for nuclear magnetic resonance sensing comprising the steps of:

providing at least one magnet having a longitudinal axis and having substantially uniform magnetization and a magnetization direction along an axis perpendicular to said longitudinal axis;

causing said at least one magnet to generate a static magnetic field of generally uniform amplitude in a region remote therefrom containing materials sought to be analyzed, said static magnetic field having a static field direction perpendicular to said longitudinal axis in said remote region;

generating a radio frequency magnetic field in said remote region for exciting nuclei of the material sought to be analyzed and having a radio frequency magnetic field direction substantially perpendicular to both said longitudinal axis and to said static field direction;

receiving nuclear magnetic resonance signals from the excited nuclei; and providing in response to the received nuclear magnetic resonance signals an output indication of properties of the material sought to be analyzed.

20. A method according to claim 19 and wherein said step of generating a static magnetic field includes the step of generating a static magnetic field in region surrounding a well bore hole.

21. A method according to claim 19 and comprising the steps of generating a static magnetic field, generating a radio frequency magnetic field and receiving nuclear magnetic resonance signals at a plurality of locations along a bore hole, thereby to enable a plurality of nuclear magnetic resonance measurements to be carried out therealong.

22. A method according to claim 19 and also comprising the step of selectably varying the frequency of said radio frequency magnetic field.

23. A method for well logging using nuclear magnetic resonance and comprising the following steps:

generating a static magnetic field substantially perpendicular to the axis of a bore hole in a region surrounding the bore hole which region includes material sought to be analyzed;

generating a radio frequency magnetic field in said region in a direction substantially perpendicular to both the axis of the bore hole and to the static magnetic field for exciting nuclei of the material sought to be analyzed; and receiving nuclear magnetic resonance signals from the excited nuclei.

24. A method according to claim 23 and also comprising the step of:

providing an output indication of properties of the material sought to be analyzed on the basis of the received nuclear magnetic resonance signals.

25. A method according to claim 23 and wherein said step of generating a static magnetic field includes generating a static magnetic field having a magnetic field amplitude gradient which extends substantially radially with respect to the axis of the bore hole.

26. A method for nuclear magnetic resonance sensing comprising the steps of:

providing at least one non-conductive permanent magnet of generally cylindrical configuration and having a longitudinal axis, the overall length of said at least one permanent magnet along said longitudinal axis being greater than its dimensions perpendicular to said longitudinal axis and greater than twice the radial separation of said remote region and said longitudinal axis, said at least one permanent magnet having substantially uniform magnetization in a direction extending substantially along a magnetization axis perpendicular to said longitudinal axis;

causing said at least one magnet to generate a static magnetic field of generally uniform amplitude which is substantially azimuthally symmetric with respect to said longitudinal axis in a generally cylindrical region centered about said longitudinal axis and remote therefrom, said region containing materials sought to be analyzed, said static magnetic field having a static field direction perpendicular to said longitudinal axis in said remote region and having a magnetic field amplitude gradient which extends substantially radially with respect to the longitudinal axis and which gradient is substantially azimuthally symmetric about the longitudinal axis;

generating a radio frequency magnetic field of generally uniform and azimuthally symmetric amplitude in said remote region for exciting nuclei of the material sought to be analyzed and having a radio frequency magnetic field direction substantially perpendicular to both said longitudinal axis and to said static field direction;

receiving nuclear magnetic resonance signals from the material sought to be analyzed; and providing in response to the received nuclear magnetic resonance signals an output indication of properties of the material sought to be analyzed.

* * * * *

UNITED STATES PATENT AND TRADEMARK OFFICE
CERTIFICATE OF CORRECTION

PATENT NO. : 4,710,713

DATED : December 1, 1987

INVENTOR(S) : Zvi Taicher, et al

It is certified that error appears in the above-identified patent and that said Letters Patent is hereby corrected as shown below:

On the title page Inventors and Assignee should read

--(75) Inventors: Zvi Taicher and Shmuel Strikman --

--(73) Assignee: Numar Corporation, Malvern, PA. --

Item (19) "Strikman" should read -- Taicher et al --.

Signed and Sealed this

Twenty-fourth Day of May, 1988

Attest:

DONALD J. QUIGG

*Attesting Officer*       *Commissioner of Patents and Trademarks*